United States Patent
Kelley, III et al.

(10) Patent No.: US 9,248,093 B2
(45) Date of Patent: Feb. 2, 2016

(54) CATHETER LOCKING SOLUTION HAVING ANTIMICROBIAL AND ANTICOAGULATION PROPERTIES

(75) Inventors: John J. Kelley, III, Glen Rock, NJ (US); Thelma I. Valdes, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 243 days.

(21) Appl. No.: 12/797,336

(22) Filed: Jun. 9, 2010

(65) Prior Publication Data

US 2010/0318040 A1 Dec. 16, 2010

Related U.S. Application Data

(60) Provisional application No. 61/186,173, filed on Jun. 11, 2009.

(51) Int. Cl.
| | |
|---|---|
| A61K 9/00 | (2006.01) |
| A61K 31/167 | (2006.01) |
| A61K 31/245 | (2006.01) |
| A61K 31/445 | (2006.01) |
| A61K 31/47 | (2006.01) |
| A61L 29/14 | (2006.01) |
| A61L 29/16 | (2006.01) |
| A61K 47/36 | (2006.01) |
| A61M 25/00 | (2006.01) |

(52) U.S. Cl.
CPC .............. *A61K 9/0019* (2013.01); *A61K 31/167* (2013.01); *A61K 31/245* (2013.01); *A61K 31/445* (2013.01); *A61K 31/47* (2013.01); *A61L 29/14* (2013.01); *A61L 29/16* (2013.01); *A61K 47/36* (2013.01); *A61L 2300/402* (2013.01); *A61L 2300/404* (2013.01); *A61L 2300/42* (2013.01); *A61M 25/00* (2013.01); *A61M 2025/0019* (2013.01); *A61M 2025/0056* (2013.01)

(58) Field of Classification Search
CPC ... A61K 9/019; A61K 31/167; A61K 31/245; A61K 31/47; A61L 29/14; A61L 29/16
See application file for complete search history.

(56) References Cited

U.S. PATENT DOCUMENTS

| 5,614,490 | A | 3/1997 | Przybelski |
|---|---|---|---|
| 5,733,869 | A | 3/1998 | Burhop et al. |
| 6,165,484 | A | 12/2000 | Raad et al. |
| 6,258,797 | B1 | 7/2001 | Lehner |
| 6,458,762 | B1 | 10/2002 | McKenzie et al. |
| 6,509,319 | B1 | 1/2003 | Raad et al. |
| 6,762,206 | B2 | 7/2004 | Khan |
| 6,958,049 | B1 | 10/2005 | Ash |
| 2001/0002258 | A1 | 5/2001 | Khan et al. |
| 2004/0034329 | A1 | 2/2004 | Mankus et al. |
| 2004/0092890 | A1 | 5/2004 | Ash |
| 2004/0156908 | A1 | 8/2004 | Polaschegg |
| 2005/0074485 | A1 | 4/2005 | Lipton |
| 2005/0124970 | A1 | 6/2005 | Kunin et al. |
| 2005/0215978 | A1 | 9/2005 | Ash |
| 2006/0094690 | A1 | 5/2006 | Prosl |
| 2006/0177477 | A1 | 8/2006 | Ash et al. |

FOREIGN PATENT DOCUMENTS

| CN | 1816330 | A | 8/2006 |
|---|---|---|---|
| EP | 0973560 | B1 | 9/2002 |
| EP | 1284780 | B1 | 2/2003 |
| EP | 1442753 | A1 | 8/2004 |
| EP | 1688154 | A1 | 8/2006 |
| EP | 1107807 | B1 | 10/2006 |
| JP | 04208857 | * | 7/1992 |
| WO | 00/10385 | A1 | 3/2000 |
| WO | 0185249 | A1 | 11/2001 |
| WO | 2004/108093 | A2 | 12/2004 |
| WO | 2006086250 | A2 | 8/2006 |
| WO | 2009/063223 | A1 | 5/2009 |

OTHER PUBLICATIONS de' Clari, Antimicrobial activity of local anesthetics, Intensive care medicine, vol. 18, No. 6 (1992), 380, DOI: 10.1007/BF01694373.*
Drug Facts, Anbesol liquid, 2007, from online: http://dailymed.nlm.nih.gov/dailymed/fda/fdaDrugXsl.cfm?id=24496&type=display.*
Markel et al, Continuous lidocaine infusion in an ambulatory patient with recurrent ventricular tachycardia, American Heart Journal, p. 184, vol. 112, Jul. 1986.*
AD Russell, PADs: drugs with antimicrobial activity, Hospital Pharmcay Europe, Jun. 2002pp. 1-3.*
Tashcuk et al, Synthesis and antimicrobial activity of quaternary salts based on bromomethylstilbenes and -tolanes and some amino ethers and esters, Chernovitsky Medical institute, vol. 12, No. 6, Jun. 1978, pp. 70-74.*
English abstract of JP 04208857, Jul. 1992.*
Siau et al. "In Vitro Effects of Local Anaesthetics on the Thromboelastographic Profile of Parturients", British Journal of Anaesthesia, 2005, p. 117-120, vol. 94 No. 1, Board of Management and Trustees of the British Journal of Anaesthesia.
Chandan et al. "Sensitivity of Respiratory Bacteria to Lignocaine", Pathology, Aug. 2005, p. 305-307, vol. 37 No. 4, Royal College of Pathologists of Australasia.
Sakuragi et al. "Bactericidal Activity of Clinically Used Local Anesthetics on *Staphylococcus aureus*", Regional Anesthesia, 1996, p. 239-242, vol. 21 No. 3.
Grimmond et al. "Antimicrobial Activity of Bupivacaine and Pethidine", Anaesthesia Intensive Care, 1986, p. 418-420, vol. 14.

(Continued)

*Primary Examiner* — Mina Haghighatian
(74) *Attorney, Agent, or Firm* — The Webb Law Firm

(57) ABSTRACT

The present invention includes a catheter locking solution having both antimicrobial and anticoagulant properties including a local anesthetic and a viscosifying agent. The local anesthetic of the present invention may be an amino amide; an amino ester; an aminoacylanilide; an aminoalkyl benzoate; an amino carbonate; an N-phenylamidine compound; an N-aminoalkyl amid; an aminoketone, or combinations and mixtures thereof. In a particular embodiment of the present invention, the local anesthetic is tetracaine or dibucaine.

29 Claims, 7 Drawing Sheets

(56) References Cited

OTHER PUBLICATIONS

Feldman et al. "Do Agents Used for Epidural Analgesia Have Antimicrobial Properties?", Regional Anesthesia, 1994, p. 43-47, vol. 19 No. 1.

Rosenberg et al. "Antimicrobial Activity of Bupivacaine and Morphine", Anesthesiology, 1985, p. 178-179, vol. 62.

Tobias et al. "Lidocaine and Bupivacaine Exert Differential Effects on Whole Blood Coagulation", Journal of Clinical Anesthesia, 1999, p. 52-55, vol. 11, Elsevier Science, New York.

Kohrs et al. "Bupivacaine Inhibits Whole Blood Coagulation In Vitro", Regional Anesthesia and Pain Medicine, 1999, p. 326-330, vol. 24 No. 4, American Society of Regional Anesthesia.

Aydin et al. "Antimicrobial Activity of Ropivacaine and Other Local Anaesthetics", European Journal of Anaesthesiology, 2001, p. 687-694, vol. 18, European Academy of Anaesthesiology.

Pere et al. "Poor Antibacterial Effect of Ropivacaine: Comparison with Bupivacaine", Anesthesiology, 1999, p. 884-886, vol. 91, American Society of Anesthesiologists, Inc.

O'Grady et al., "Guidelines for the Prevention of Intravascular Catheter-Related Infections", Morbidity and Mortality Weekly Report, Centers for Disease Control, 2002.

Raad, "Intravascular-Catheter-Related Infections", The Lancet, 1998, vol. 351, pp. 893-898. (Review of Article by Panagea et al.).

Meyer, "Antimicrobial Properties of Bupivacaine", Anaesth Intensive Care, 1997, vol. 25(2), p. 200. (Abstract only).

Okuno et al., "The Influence of Local Anesthetics on Human Leukocyte Functions Studied by Micro Whole Blood Collection and Flowcytometry", Masui, 1996, vol. 45(3), pp. 317-325. (Abstract only).

Kampe et al., "Ropivacaine 0.1% with Sufentanil 1 Microg/mL Inhibits In Vitro Growth of Pseudomonas Aeruginosa and Does Not Promote Multiplication of *Staphylococcus aureus*", Anesthesia and Analgesia, 2003, vol. 97(2), pp. 409-411.

Mikawa et al., "Effects of Ropivacaine on Human Neutrophil Function: Comparison with Bupivacaine and Lidocaine", European Journal of Anaesthesiology, 2003, vol. 20(2). (Abstract only).

Nitescu, et al., "Bacteriology, Drug Stability and Exchange of Percutaneous Delivery Systems and Antibacterial Filters in Long-Term Intrathecal Infusion of Opioid Drugs and Bupivacaine in 'Refractory' Pain", Clinical Journal of Pain, 1992, vol. 8(4). (Abstract only).

Simon et al., "Inhibition of RNA Synthesis in *Escherichia coli* by Levorphanol", Proceedings of the National Academy of Sciences USA, 1964, vol. 51, pp. 877-883.

Tamanai-Shacoori et al., "Sufentanil Modifies the Antibacterial Activity of Bupivacaine and Ropivacaine", Canadian Journal of Anaesthesia, 2004, vol. 51(9), pp. 911-914.

Sakuragi et al., "Bactericidal Activity of 0.5% Bupivacaine with Preservatives on Microorganisms in the Human Skin Flora", Reg. Anesth., 1997, vol. 22(2). (Abstract only).

Tobias et al., "Lidocaine Inhibits Blood Coagulation: Implications for Epidural Blood Patch", Anesth. Analg., 1996, vol. 82(4), pp. 766-769.

Pina-Vaz et al., "Antifungal Activity of Local Anesthetics Against *Candida* Species", Infectious Diseases in Obstetrics and Gynecology, 2000, vol. 8(3-4), pp. 124-137.

Capdevila et al., "Lack of Antimicrobial Activity of Sodium Heparin for Treating Experimental Catheter-Related Infection Due to *Staphylococcus aureus* Using the Antibiotic-Lock Technique", Clin. Microbiol. Infect., 2001, vol. 7(4), pp. 206-212.

Shah et al., "Antimicrobial Activity of a Novel Catheter Lock Solution", Antimicrobial Agents and Chemotherapy, 2002, vol. 46(6), pp. 1674-1679.

Shanks et al., "Heparin Stimulates *Staphylococcus aureus* Biofilm Formation", Infection and Immunity, 2005, vol. 73 (8), pp. 4596-4606.

Johnson, et al., "Local Anesthetics as Antimicrobial Agents: A Review", Surgical Infections, 2008, vol. 9, No. 2.

Hu Ge et al., "Influence of anesthesia on coagulation function", Int. J. Anesth. Resus., vol. 28, No. 5, Oct. 31, 2007, English abstract only.

\* cited by examiner

*Staphylococcus epidermidis* counts as percent of control

*Staphylococcus epidermidis* biofilm eradication on silicone catheter segments

Candida albicans biofilm eradication on silicone catheter segments

CATHETER LOCKING SOLUTION HAVING ANTIMICROBIAL AND ANTICOAGULATION PROPERTIES

CROSS REFERENCE TO RELATED APPLICATIONS

This application claims priority to U.S. Provisional Patent Application No. 61/186,173, filed Jun. 11, 2009, entitled "A Catheter Locking Solution Having Antimicrobial and Anticoagulation Properties", the entire disclosure of which is herein incorporated by reference.

BACKGROUND OF THE INVENTION

1. Field of the Invention

The present invention relates to the maintenance of catheters in a condition that is substantially free of microbial colonization. Specifically, the invention pertains to the use of a solution having both antimicrobial and anticoagulant properties disposable within the lumen of a catheter.

2. Description of Related Art

Catheters, particularly intravenous (IV) catheters, may be used for infusing fluid, such as a medication, into a patient or withdrawing fluid, such as blood, from a patient. Catheters may include a lumen or reservoir which contains fluid or medication to be injected into, or removed from, a patient's body. In certain configurations an injection port may be provided with the catheter.

Complications associated with catheters include those related to their insertion, such as pneumo/hemothorax, arterial puncture and nerve injury, and those occurring as a consequence of their use, such as thrombosis, infection, and clotting. Catheter occlusions will often occur due to thrombotic complications related to the formation of a fibrin sheath within the lumen of the catheter. Formation of a fibrin sheath may allow for adherence of bacteria to the interior of the catheter lumen and serve as a locus for catheter related infection.

In order to avoid the complication of catheter occlusions between uses, catheters may be filled with a lock solution that includes a concentrated solution of the commonly used anticoagulant heparin. A heparin lock solution fills the entire lumen of a catheter with the solution. The heparin lock solution is injected into the catheter lumen immediately after each use, and is preferably left within the catheter until the catheter is accessed again. The heparin lock solution must be withdrawn from the catheter before the next use so that the heparin lock solution is not introduced into the body of the patient. Typically, heparin lock solutions include up to 10,000 units of heparin per catheter lumen. Infusing this amount of heparin into a patient may result in excessive bleeding.

However, even with the use of a traditional heparin lock solution, the catheter can become occluded between uses from coagulation of blood within the catheter. Blood may be present within the catheter because an inadequate volume of heparin was infused within the catheter lumen, the heparin lock solution diffused from the lumen, or residual blood remains in the lumen. This often results in formation of a thrombus with concomitant loss of flow through the lumen.

Heparin has no substantial antibacterial properties and, in fact, may help to promote growth of bacteria within the biofilm layer of protein on the catheter surfaces. The biofilm proteins on the catheter surfaces can protect bacteria growing within a catheter lumen from antibiotics and white blood cells. Heparin has also been found to induce the loss of platelets and can induce clotting in some patients.

To avoid the complication of catheter occlusions between uses, certain catheters may be filled with lock solutions that include citrate salts such as sodium citrate. While sodium citrate is a known anticoagulant, equivalent to about 20 units/mL of heparin (per internal testing), it does not have antimicrobial activity at low concentration (<10%). This is a problem since administering sodium citrate in high concentrations may result in patient toxicity.

If a catheter implanted within a patient becomes infected, the patient may require additional systemic antibiotic treatment and/or removal of the catheter. The risks of catheter-related infections may vary according to the duration of catheter placement within the body, the site of insertion, anatomic location of blood vessels, improper catheter insertion techniques, and the use of improper types of catheter material.

The majority of serious catheter-related infections are associated with central venous catheters, especially those that are placed in patients in an intensive care unit (ICU). In the ICU setting, the incidence of infection is often higher than in the less acute in-patient or ambulatory setting. Certain catheters, such as pulmonary artery catheters and peripheral arterial catheters, may be accessed multiple times per day for hemodynamic measurements or to obtain samples for laboratory analysis, augmenting the potential for contamination and subsequent clinical infection.

Examples of pathogens most commonly related to catheter related bloodstream infections (CR-BSI) include coagulase-negative organisms, gram-positive pathogens, gram-negative pathogens, and fungal organisms. Specific examples of gram-positive pathogens include *Staphylococci* organisms, such as *Staphylococcus aureus* and *Staphylococcus epidermidis*, species of *Enterococci*, and species of *Bacillus*. Gram-negative pathogens include: *Pseudomonas aeruginosa, Pseudomonas cepacia E. coli*, and species of *Klebsiella*. Examples of fungal microorganisms commonly related to CR-BSI, include species of *Candida*, such as *Candida albicans*.

In addition, bacterial species are rapidly acquiring resistance to antibiotic therapy including methicillin-resistant *S. aureus*, vancomycin-intermediate *S. aureus*, and vancomycin resistant *enterococci*.

Once microbial pathogens colonize the interior surface of a catheter lumen, the pathogens may embed in a self-produced extracellular polymeric matrix. Within this matrix, pathogens are protected from host defense and from traditional antibiotics.

Accordingly, a need exists for alternative methods to prevent microbial pathogens from colonizing catheters that additionally provide anticoagulant properties.

SUMMARY OF THE INVENTION

One embodiment of the present invention is directed towards a catheter locking solution that includes a local anesthetic and a viscosifying agent.

Specifically, the catheter locking solution of the present invention may include a local anesthetic and a viscosifying agent, wherein the local anesthetic includes an amino amide; an amino ester; an aminoacylanilide; an aminoalkyl benzoate; an amino carbonate; an N-phenylamidine compound; an N-aminoalkyl amid; an aminoketone, or combinations and mixtures thereof. The local anesthetic may be selected from the group consisting of dibucaine, tetracaine, bupivacaine, ropivacaine, etidocaine, lidocaine, prilocaine, procaine, novocaine, choloroprocaine, propoxycaine, chlorocaine, mepivacaine, xylocaine, benzocaine, chloroprocaine, cyclomethycaine, dimethocaine, popoxycaine, proparacaine, articaine, carticaine, levobupivacaine, piperocaine, trimecaine, hexylcaine, benoxinate, butucaine, diperodon, phenacaine, falicaine, dyclonine, pramoxine, dimethisoquien, and combinations and mixtures thereof and can be present in an amount of 0.05 mg/mL-100 mg/mL, for example, in an amount of 0.24 mg/mL-28.2 mg/mL.

The viscosifying agent may be polyethylene glycol, glycerin, polygeline, dextran, or any mixture thereof. In particular, the local anesthetic may be tetracaine and the viscosifying agent may be polyethylene glycol, or the local anesthetic may be dibucaine and the viscosifying agent may be polyethylene glycol. The local anesthetic may be present in the catheter locking solution in a concentration, in weight percent, of between 0.001%-99.99%, and the viscosifying agent may be present in a concentration, in weight percent, of between 0.001%-99.99%. The catheter locking solution may also include an additional antimicrobial agent and/or an additional anticoagulation agent.

Another embodiment of the present invention is directed towards a method for inhibiting antimicrobial activity and coagulation in a catheter and includes providing a catheter defining a lumen, and infusing the lumen of the catheter with a catheter locking solution including a local anesthetic and a viscosifying agent.

The lumen of the catheter may be reinfused with the catheter locking solution after a designated time, for example, less than one week. Additionally, the lumen of the catheter may have an internal volume and the lock solution may be infused into the lumen, such that the lock solution fills between about 80% and about 100% of the internal volume of the lumen. The lumen of the catheter may be infused between 1 and 1000 times.

Another embodiment of the present invention is directed towards a pre-filled syringe. The pre-filled syringe includes a locking solution including a local anesthetic and a viscosifying agent.

The catheter locking solution contained in the pre-filled syringe of the present invention may include a local anesthetic and a viscosifying agent, wherein the local anesthetic includes an amino amide; an amino ester; an aminoacylanilide; an aminoalkyl benzoate; an amino carbonate; an N-phenylamidine compound; an N-aminoalkyl amid; an aminoketone, or combinations and mixtures thereof. The local anesthetic may be selected from the group consisting of dibucaine, tetracaine, bupivacaine, ropivacaine, etidocaine, lidocaine, prilocaine, procaine, novocaine, choloroprocaine, propoxycaine, chlorocaine, mepivacaine, xylocaine, benzocaine, chloroprocaine, cyclomethycaine, dimethocaine, popoxycaine, proparacaine, articaine, carticaine, levobupivacaine, piperocaine, trimecaine, hexylcaine, benoxinate, butucaine, diperodon, phenacaine, falicaine, dyclonine, pramoxine, dimethisoquien, and combinations and mixtures thereof and can be present in an amount of 0.05 mg/mL-100 mg/mL, for example, in an amount of 0.24 mg/mL-28.2 mg/mL.

The viscosifying agent may be polyethylene glycol, glycerin, dextran, or polygeline. In particular, the local anesthetic may be tetracaine and the viscosifying agent may be polyethylene glycol, or the local anesthetic may be dibucaine and the viscosifying agent may be polyethylene glycol. The local anesthetic may be present in the catheter locking solution in a concentration, in weight percent, of between 0.001%-99.99%, and the viscosifying agent may be present in a concentration, in weight percent, of between 0.001%-99.99%. The catheter locking solution contained in the pre-filled syringe may also include an additional antimicrobial agent and/or an additional anticoagulation agent.

Another embodiment of the present invention is directed to a catheter including a tube defining lumen therethrough, wherein at least a portion of the lumen is infused with a catheter locking solution. The catheter locking solution includes a local anesthetic having anticoagulant and antimicrobial activity and a viscosifying agent.

Specifically, the catheter locking solution of the present invention may include a local anesthetic and a viscosifying agent, wherein the local anesthetic includes an amino amide; an amino ester; an aminoacylanilide; an aminoalkyl benzoate; an amino carbonate; an N-phenylamidine compound; an N-aminoalkyl amid; an aminoketone, or combinations and mixtures thereof. The local anesthetic may be selected from the group consisting of dibucaine, tetracaine, bupivacaine, ropivacaine, etidocaine, lidocaine, prilocaine, procaine, novocaine, choloroprocaine, propoxycaine, chlorocaine, mepivacaine, xylocaine, benzocaine, chloroprocaine, cyclomethycaine, dimethocaine, popoxycaine, proparacaine, articaine, carticaine, levobupivacaine, piperocaine, trimecaine, hexylcaine, benoxinate, butucaine, diperodon, phenacaine, falicaine, dyclonine, pramoxine, dimethisoquien, and combinations and mixtures.

An additional embodiment of the present invention is directed towards a catheter locking solution including a local anesthetic having anticoagulant and antimicrobial activity, and a viscosifying agent. The local anesthetic is dibucaine and is present in an amount of 0.24 mg/mL-28.2 mg/mL. The viscosifying agent is polyethylene glycol.

Another additional embodiment of the present invention is directed towards a catheter locking solution including a local anesthetic having anticoagulant and antimicrobial activity, and a viscosifying agent. The local anesthetic is tetracaine and is present in an amount of 0.24 mg/mL-28.2 mg/mL. The viscosifying agent is polyethylene glycol.

DETAILED DESCRIPTION OF THE INVENTION

Figure 1:
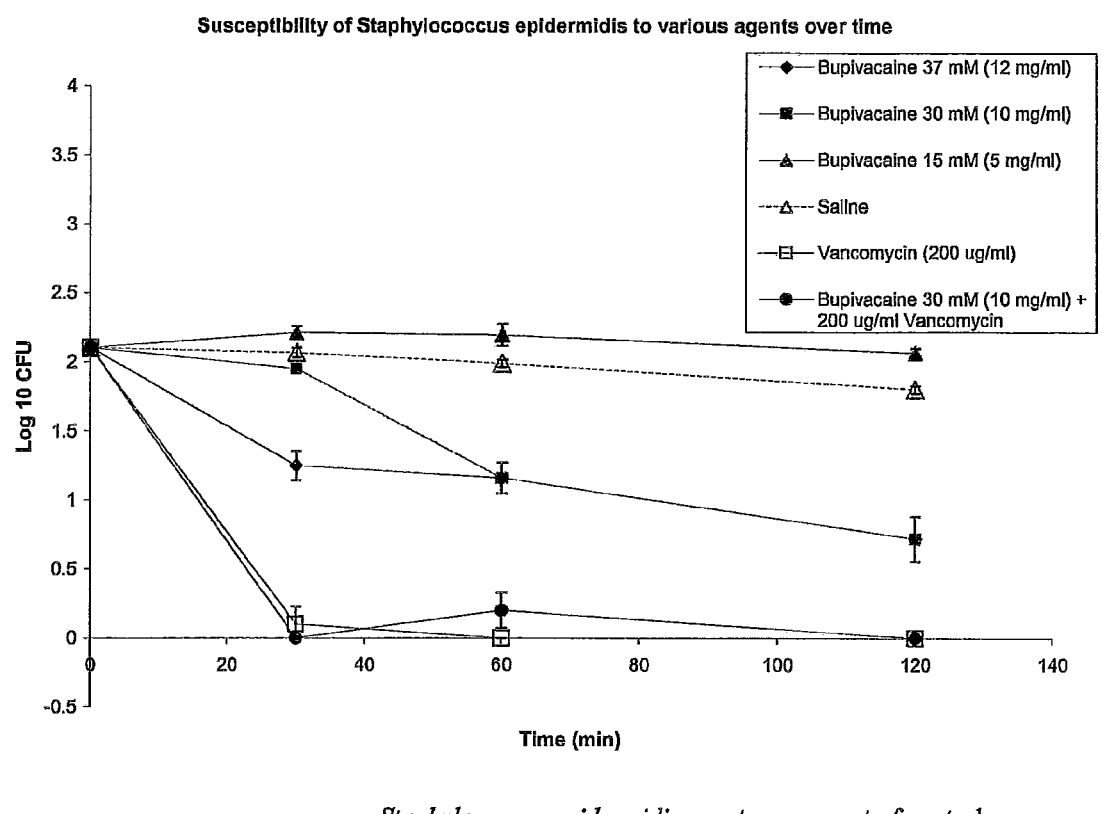
FIG. 1 is a graphical representation of the susceptibility of *Staphylococcus epidermidis* to various agents over time in accordance with the present invention.

In one embodiment, the present invention provides a catheter locking solution including a local anesthetic and a viscosifying agent. The lock solution of the present invention may enhance the patency (the state of being open or unobstructed) of the catheter and exhibits anticoagulation and antibiotic activity. The lock solution of the present invention may provide particular advantages by increasing the longevity of catheters, reducing incidence of catheter occlusion, or reducing incidence of sepsis or bacterial infection in the patient.

As used herein, the term "lock solution" or "locking solution" refers to a solution that is injected or otherwise infused into a lumen of a catheter with the intention of allowing a substantial portion of the solution to remain in the lumen until it is desired or required to access or re-access the lumen, typically for additional treatment. Additional treatment may include, for example, infusion or withdrawal of fluid into the lumen of a catheter. The locking solution may be placed into the catheter to provide short or long-term protection. Preferably, the lock solution can remain in the lumen for a desired amount of time lasting to about one week. However, the lock solution may be changed on a daily basis, such as during regular care or sterile maintenance of the catheter. The catheter may be changed or refreshed by aspirating the lock solution out of the catheter lumen, and locking the catheter with new catheter lock solution within the catheter for a desired amount of time. Use of a lock solution of the present invention may prolong the lifetime of the catheter, lengthen the interval between required replacements of the lock solution, or inhibit infection in a patient.

As used herein, the term "local anesthetic" means a compound or solution that causes reversible local numbness and/or analgesia and a loss of nociception, specifically the neural processes of encoding and processing noxious stimuli. Local anesthetics suitable for use with the present invention generally belong to one of two classes: amino amide and amino ester local anesthetics. However, other classes and subclasses of local anesthetics may be suitable for use with the present invention, including but not limited to, aminoacylanilide compounds and related compounds having various substituents on the ring system or amine nitrogen; aminoalkyl benzoate compounds; amino carbonate compounds; N-phenylamidine compounds; N-aminoalkyl amid compounds; aminoketone compounds; and amino ester compounds. In one embodiment of the present invention, the local anesthetic can be an amino amide, and in another embodiment of the present invention, the local anesthetic can be an amino ester. Alternatively, the local anesthetic can be a mixture of an amino amide and an amino ester.

Examples of local anesthetics suitable for use with the present invention include: dibucaine, tetracaine, bupivacaine, ropivacaine, etidocaine, lidocaine, prilocaine, procaine, novocaine, choloroprocaine, propoxycaine, chlorocaine, mepivacaine, xylocaine, benzocaine, chloroprocaine, cyclomethycaine, dimethocaine, popoxycaine, proparacaine, articaine, carticaine, levobupivacaine, piperocaine, trimecaine, hexylcaine, benoxinate, butucaine, diperodon, phenacaine, falicaine, dyclonine, pramoxine, dimethisoquien, and combinations and mixtures thereof.

The catheter locking solution may include the local anesthetic in an amount of 0.05 mg/mL-100 mg/mL, such as, in an amount of 0.1 mg/mL-50 mg/mL. In another embodiment, the locking solution may include the local anesthetic in an amount of 0.24 mg/mL-28.2 mg/mL, such as in an amount of 0.59 mg/mL-18.8 mg/mL. In another embodiment the locking solution may include the local anesthetic in an amount of 0.94 mg/mL-4.75 mg/mL. In a further embodiment, a viscosifying agent accounts for the remainder of the catheter locking solution.

The lock solution has a viscosity sufficient to maintain the lock solution in the lumen for a desired amount of time. Without the viscosifying agent, the viscosity of the lock solution is close to the viscosity of water, 1 MPa·s. The viscosity of the locking solution can be increased by using a viscosifying agent. By increasing the viscosity of the lock solution such that it is closer to that of blood, the lock solution may be prevented from aspirating from the catheter lumen, and into the surrounding blood environment. Preferably, the lock solution has a viscosity that is close to the viscosity that is equal to or less than the viscosity of blood, for example, less than or equal to about 4 MPa·s, or less than or equal to about 3 MPa·s.

Viscosifying agents suitable for use with the present invention include pharmaceutically acceptable agents known or commonly used in treatment of animals, including humans. The term "pharmaceutically acceptable" means a compound, solution, or mixtures suitable for use in contact with tissues of humans and lower animals without undue toxicity, irritation, or allergic response. Examples of viscosifying agents include, but are not limited to, polyethylene glycol, glycerin, polygeline, dextran, or some mixture of polyethylene glycol, glycerin, polygeline, and dextran. Other viscosifying agents capable of use with the present invention include povidone, polyvinylpyrrolidone, polyethylene glycol alginate, sodium alginate, chitosan, cabopol, starch, methylcellulose, carboxypolymethylene, carboxymethyl cellulose, hydroxypropylcellulose, non-metabolizable sugars such as sorbitol and mannitol, dextran, or any mixture thereof.

The catheter locking solution including the local anesthetic and the viscosifying agent may provide antimicrobial and anticoagulation activity thereby providing protection to a patient having a catheter inserted or implanted into a portion of the patient's body, such as a vein or other blood vessel.

Particularly, a single local anesthetic can have dual functionality as an antimicrobial agent and an anticoagulation agent. This is a significant improvement over current attempts to maintain catheters patent and free of infection, in which antibiotics and other chelators (such as EDTA or citrate) are utilized simultaneously. A single component with dual functionality eases product development, manufacturing, and clinical practice of lock solutions.

Particularly, the local anesthetic of the present invention may be an antimicrobial agent that provides antimicrobial activity. The term "antimicrobial agent", as used herein, means an agent that provides "antimicrobial activity". "Antimicrobial activity" as used herein means the destruction, inhibition, or prevention of the propagation, growth, or multiplication of unwanted organisms. The term "organisms" includes, but is not limited to, microorganisms, bacteria, undulating bacteria, spirochetes, spores, spore-forming organisms, gram-negative organisms, gram-positive organisms, yeasts, fungi, molds, viruses, aerobic organisms, anaerobic organisms, and mycobacteria. Specific examples of such organisms include the fungi *Aspergillus niger, Aspergillus flavus, Rhizopus nigricans, Cladosporium herbarium, Epidermophyton floccosum, Trichophyton mentagrophytes, Histoplasma capsulatum*, and the like; bacteria such as *Pseudomonas aeruginosa, Escherichia coli, Proteus vulgaris, Staphylococcus aureus, Staphylococcus epidermis, Streptococcus faecalis, Klebsiella, Enterobacter aerogenes, Proteus mirabilis*, other gram-negative bacteria and other gram-positive bacteria, mycobactin, and the like; and yeast such as *Saccharomyces cerevisiae, Candida albicans*, and the like. Additionally, spores of microorganisms and viruses are considered to be organisms within the scope of the present invention.

Additionally, the local anesthetic of the present invention having a local anesthetic and viscosifying agent may be an anticoagulation agent that provides anticoagulant activity. The term "anticoagulation agent", as used herein, means an agent that provides "anticoagulant activity". As used herein "anticoagulant activity" means the inhibition or prevention of blood coagulation.

The locking solution of the present invention can be used with or without additional anticoagulant agents and/or other antibacterial agents. Therefore, in one embodiment of the present invention, the catheter lock solution may also include an additional antimicrobial agent or anticoagulant agent or both. Such antibacterial and antimicrobial agents are well known to those skilled in the art and can include, without limitation, gentamicin, vancomycin, sodium citrate salts, and mixtures of these agents. Additional anticoagulant agents include, for example, heparin, urokinase, tissue plasminogen activation (tPA), and mixtures of these agents.

As described above, the locking solution of the present invention may be used to inhibit antimicrobial activity and coagulation in a catheter thereby enhancing the patency of a catheter. A catheter, as defined by the present invention, is a tube defining a lumen therethrough that may be inserted into part of the body or provided in communication with a body or other biological culture to deliver a fluid thereto or remove a fluid therefrom. In one embodiment, the catheter locking solution of the present invention may be used to inhibit antimicrobial activity and coagulation of a thin, flexible tube, such as a soft catheter or alternatively a solid tube, such as a hard catheter. The catheter locking solution of the present invention may also may be used to inhibit antimicrobial activity and coagulation of catheters that are placed into particular parts of the body to allow, for example, drainage of urine from the urinary bladder as in urinary catheterization; drainage of fluid collections; administration of intravenous fluids, medication, or prenatal nutrition; angioplasty; angiography; balloon septostomy; and direct measurement of blood pressure in an artery or vein. While the catheter locking solution of the present invention may be used to inhibit antimicrobial activity and coagulation of any catheter, the catheter locking solution may be used to inhibit antimicrobial activity and coagulation of catheters that are used, for example, for hemodialysis and hemofiltration that rely on separate draw and return catheters implanted into a vein to allow extracorporeal treatment of the blood or for peritoneal dialysis, which relies on a single catheter implanted in the peritoneum to permit introduction and withdrawal of dialysate to permit in situ dialysis.

The catheter locking solution of the present invention may be used to inhibit antimicrobial activity and coagulation of any catheter, for example, catheters used for intravenous administration of fluids and medication, including peripheral venous catheters (PVC); peripheral arterial catheters; midline catheters; noritunneled central venous catheters (CVC); pulmonary artery catheters; percutaneously inserted central catheters (PICC); tunneled catheters; totally implantable catheters; and umbilical catheters. PVCs are used predominantly in peripheral veins or veins not in the chest or abdomen, such as arm and hand veins, leg and foot veins, as well as scalp veins.

In situations where the patient requires longer treatment with an IV, the catheter locking solution of the present invention may be used to inhibit antimicrobial activity and coagulation of a catheter that will be inserted into a larger vein, for example, a subclavian vein or a jugular vein. Longer treatment catheters may be CVCs which extend into the superior vena cava to allow faster access to the bloodstream in the administration of medication and fluids, and can remain in place for up to seven days. CVCs that are required to remain in place for several weeks can be implanted or tunneled under the skin and positioned within a large vein.

Longer-term central vein catheters such as PICC can also be inserted into the cubital fossa, which then extends up into the superior vena cava, and can remain in the same vein for several weeks. PICC catheters are commonly used in the hospital setting such as intensive care units and critical care, but are also widely used in the home nursing environment and are used for patients who will require long-term therapy, for example, from several weeks to months.

The locking solution of the present invention can be used in a method for inhibiting antimicrobial activity and coagulation in a catheter, including the steps of providing a catheter having an interior surface and an exterior surface, and infusing into at least a portion of the interior surface with the catheter locking solution. Preferably, the locking solution is infused into the interior surface such that the interior surface is substantially filled. Non-limiting examples of interior surfaces of the catheter that can be coated or filled with the catheter locking solution of the present invention include the lumen, related tubing, plungers, caps, and extension sets. Other devices capable of being coated or filled with the catheter locking solution of the present invention include the inner lumen of vascular access devices, as well as needle-less access devices. The locking solution can be infused by any conventional method well known to those skilled in the art, such as dipping, spraying, or injecting.

When the lock solution of the present invention is infused into the interior surface of the catheter, a sufficient amount of the lock solution can be injected to fill or substantially fill the interior surface of the catheter as well as any adjacent surfaces or lumens of any attached access device. Alternatively, a volume less than the amount of fluid needed to fill the catheter can be infused into the interior surface. For example, a sufficient amount of lock solution can be infused into the catheter to fill, for example, from 80% to 100% of the internal volume of the catheter. In yet another embodiment, an amount greater than the internal volume of the catheter can be infused. For example, an amount of the lock solution greater than the internal volume of the catheter can be infused into the lumen, without adverse effects on the clotting system of the patient.

Depending on the local anesthetic utilized in the locking solution, the locking solution may be infused or flushed into the catheter between 1 and 1000 times. The catheter locking solution of the present invention can be prepared with simple mixing at room temperature and can provide antimicrobial and anticoagulation activity for a period of about one week.

In one embodiment, the catheter includes a tube defining lumen therethrough that is pre-filled with the catheter locking solution of the present invention prior to insertion within the patient.

Figure 5:
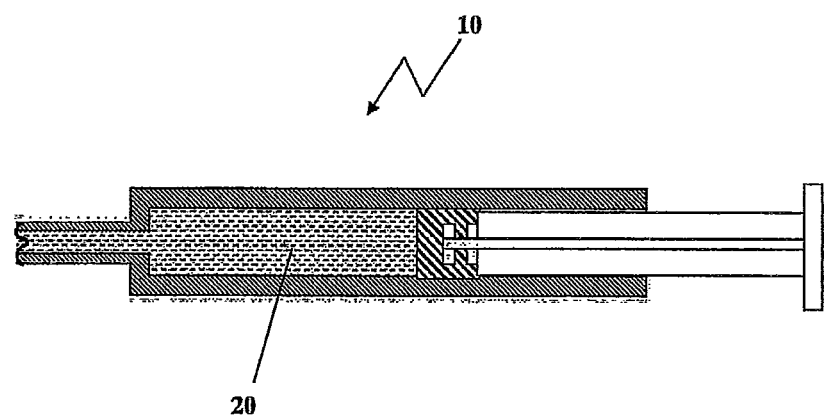
FIG. 5 is a longitudinal cross-sectional view of a pre-filled syringe including the catheter locking solution of the claimed invention.

Alternatively, the lock solution may be provided in an infusion device, such as a pre-filled syringe 10 shown in FIG. 5 containing the catheter locking solution 20 of the present invention. As contemplated herein, any conventionally known syringe may be used with the locking solution of the present invention.

Whereas particular embodiments of this invention have been described above for purposes of illustration, it will be evident to those skilled in the art that numerous variations of the details of the present invention may be made without departing from the invention as defined in the appended claims.

EXAMPLES

To illustrate the antimicrobial efficacy of selected local anesthetics in the lock solution of the present invention, three different tests were conducted and are explained below.

Pathogenic species chosen for the experiments are shown in Table 1. *Staphylococcus epidermidis* is a coagulase-negative and gram-positive bacterial species, *Candida albicans* is a fungal species, and *Pseudomonas aeruginosa* is a gram-negative bacterial species. As noted above, these are representative strains in Catheter Related-Blood Stream Infections (CR-BSI). The anesthetics (commercially available, for example, from Sigma-Aldrich Co.) chosen for efficacy testing are listed in Table 2.

TABLE 1

List of pathogenic species chosen

| Organism | Organism Type | ATCC Deposit Number |
| --- | --- | --- |
| *Staphylococcus epidermidis* | Gram-positive | 12228 |
| *Candida albicans* | Fungal | 10231 |
| *Pseudomonas aeruginosa* | Gram-negative | 27853 |

TABLE 2

Listed of anesthetics included in testing

| Compound | Product Number | Chemical Structure |
| --- | --- | --- |
| Bupivacaine HCl | B5274 | 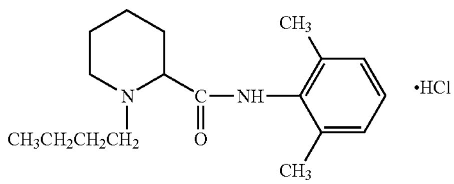 |
| Dibucaine HCl | D0638 | 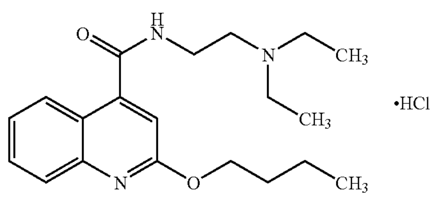 [SMILES: CCCCOc1cc(C(=O)NCCN(CC)CC)c2ccccc2n1 ; Cl] |
| Mepivacaine HCl | M3189 | 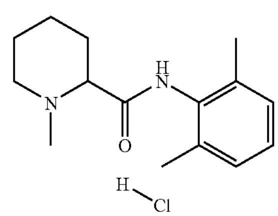 |
| Prilocaine HCl | P9547 | 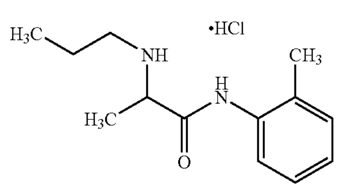 [SMILES: Cl ; CCCNC(C)C(=O)Nc1ccccc1C] |
| Tetracaine HCl | T3937 | 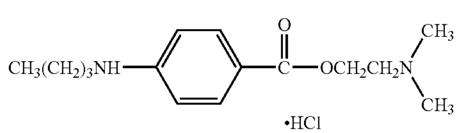 |

Three types of tests were conducted to demonstrate the antimicrobial efficacy of these anesthetics in the lock solution of the present invention. These are: A) tests conducted on cells in suspension or planktonic cells; B) tests conducted to prevent biofilm formation (minimum biofilm inhibitory concentration); and C) tests conducted on established biofilms on a simulated catheter model.

A. Planktonic Cell Tests

In the planktonic cell tests, bupivacine was tested against non-adhering coagulase negative *S. epidermidis*, which is the bacterial species most prominent in the pathogenesis of CR-BSI. The planktonic cell experiments were performed by the following procedures. First, bacterial suspensions were prepared. Particularly, using BD BBL™ Qualiswab™, *S. epidermidis* was plated on a Tryptic Soy Broth (TSB) Petri Dish and grown overnight at 37° C. Using a sterile loop, a colony of *S. epidermidis* was picked up from the TSB Petri Dish and placed into a sterile flask containing 25 mL of sterile TSB media. The flask was then placed in a 37° C. shaking incubator and was shaken at 150 RPM overnight. The next day, 15 mL of the prepared bacterial suspension was placed into an autoclaved centrifuge tube and centrifuged at 10,000 RPM for 10 minutes using a Sorval Centrifuge. The bacteria from the bacterial suspension were rinsed in 0.9% saline by discarding the liquid media (after centrifugation step) and by resuspending the microbial pellet in 20 mL of sterile 0.9% saline. The bacteria were centrifuged and rinsed twice more, for a total of three saline rinses.

The bacteria were centrifuged once more, and resuspended in 10 mL of 0.9% saline. The concentration of the bacterial suspension was checked using a nephelometer, in which a suspension equal to a 0.5 MacFarland standard, is equivalent to ~$1\times10^8$ CFU/mL. Two serial 100× dilutions were prepared in 0.9% saline, 50 mL final volume for each, for a concentration of $1\times10^4$ CFU/mL. A 10× dilution was then prepared in 0.9% saline, 50 mL final volume for a final concentration of $1\times10^3$ CFU/mL.

Bulk concentrations of the bupivacaine and/or vancomyacin (as noted in FIG. 1) were prepared in separate beakers and were filter sterilized. Three replicate test tubes per drug concentration were prepared by adjusting to the desired drug concentrations with 0.9% saline for a total volume of 4 mL. Three replicate control tubes were prepared containing 4 mL of 0.9% saline. The samples were then inoculated with 1 mL of the prepared bacterial suspension and incubated in the incubator shaker at 37° C. The cells were exposed to various local anesthetic formulations for three time periods, namely, 30, 60, and 120 minutes, at which time, 100 µl of drug/bacterial suspension were plated onto a TSB agar plate. Three replicates per tube were made to obtain colony forming units. Samples were also assessed at time 0, in which there was no exposure to antimicrobials.

FIG. 1 shows *Staphylococcus epidermidis* logarithmic counts, with 95% confidence interval values, represented by error bars. In the present example, the lethal activity, or the reduction of the organism is expressed in terms of rate of organisms killed by a fixed concentration of material. These results indicate that bupivacaine in combination with vancomyacin at 200 µg/mL was a highly effective microbial agent against *Staphylococcus epidermidis*. Bupivacaine, at the 12 mg/mL concentration, also exhibits a significant antimicrobial effect at both 30 and 60 minutes. Specifically, these results show that while the heparin and saline solutions have virtually no antimicrobial effect against *Staphylococcus epidermidis*, bupivacaine at 12 mg/mL has a substantial effect at both 30 and 60 minutes. The planktonic cell tests demonstrate the antimicrobial efficacy of the local anesthetics of the present catheter locking solution, specifically bupivacaine, at various concentrations.

B. Minimum Biofilm Inhibitory Concentration (MBIC) Tests

To further evaluate the efficacy of local anesthetics in antimicrobial lock solutions of the present invention, the minimum concentration at which these drugs can inhibit biofilm growth was tested. The local anesthetics identified in Table 4 were tested against three different species of bacteria identified in Table 3 to assess the antimicrobial efficacy against adhered microbes. It is known that adhered microbes, or biofilms, can be more resistant to antimicrobials than planktonic cells.

TABLE 3

Time required to enter log phase of microbial growth

| Bacterial Species | Approximate time required to enter log phase |
| --- | --- |
| Staphylococcus epidermidis | 3-4 hrs |
| Candida albicans | 18 hrs |
| Pseudomonas aeruginosa | 2-3 hrs |

TABLE 4

MBIC for local anesthetics in lock solutions

| | MBIC (mg/mL) | Assuming 2 mL lock volume (mg) |
| --- | --- | --- |
| *S. epidermidis* | | |
| Bupivacaine | 8.12 | 16.24 |
| Dibucaine | 0.59 | 1.18 |
| Mepivacaine | 28.2 | 56.4 |
| Tetracaine | 0.94 | 1.88 |
| *P. aeruginosa* | | |
| Bupivacaine | 16.25 | 32.5 |
| Dibucaine | 4.75 | 9.5 |
| Mepivacaine | 28.2 | 56.4 |
| Tetracaine | 6.41 | 12.82 |
| *C. albicans* | | |
| Bupivacaine | No inhibition | No inhibition |
| Dibucaine | 0.59 | 1.18 |
| Mepivacaine | No inhibition | No inhibition |
| Tetracaine | 0.24 | 0.48 |

The catheter lock solutions were evaluated at decreasing concentrations as they may undergo some dilution at the catheter tip.

Experiments were conducted against adhered microbes as follows: first, a test tube containing 10 mL of sterile TSB was inoculated with BD BBL™ Qualiswab™, with the strain of interest. The tube was placed in an incubator at 37° C. overnight. The next day, a flask containing 25 mL of sterile TSB (or Sabouraud Dextrose Broth (SDB) for fungal species) was inoculated with 1 mL of bacterial suspension. The flask was placed in an incubator at 37° C. and shaken at 150 RPM. The next day a new flask containing 25 mL of TSB (or SDB) media was inoculated with 1 mL from the previous culture. The bacterial or fungal species were allowed to grow to log phase. Specifically, as seen in Table 3, the growth times for *Staphylococcus epidermidis* was 3-4 hrs, *Candida albicans* 18 hrs, and *Pseudomonas aeruginosa* 2-3 hrs.

Figure 2:
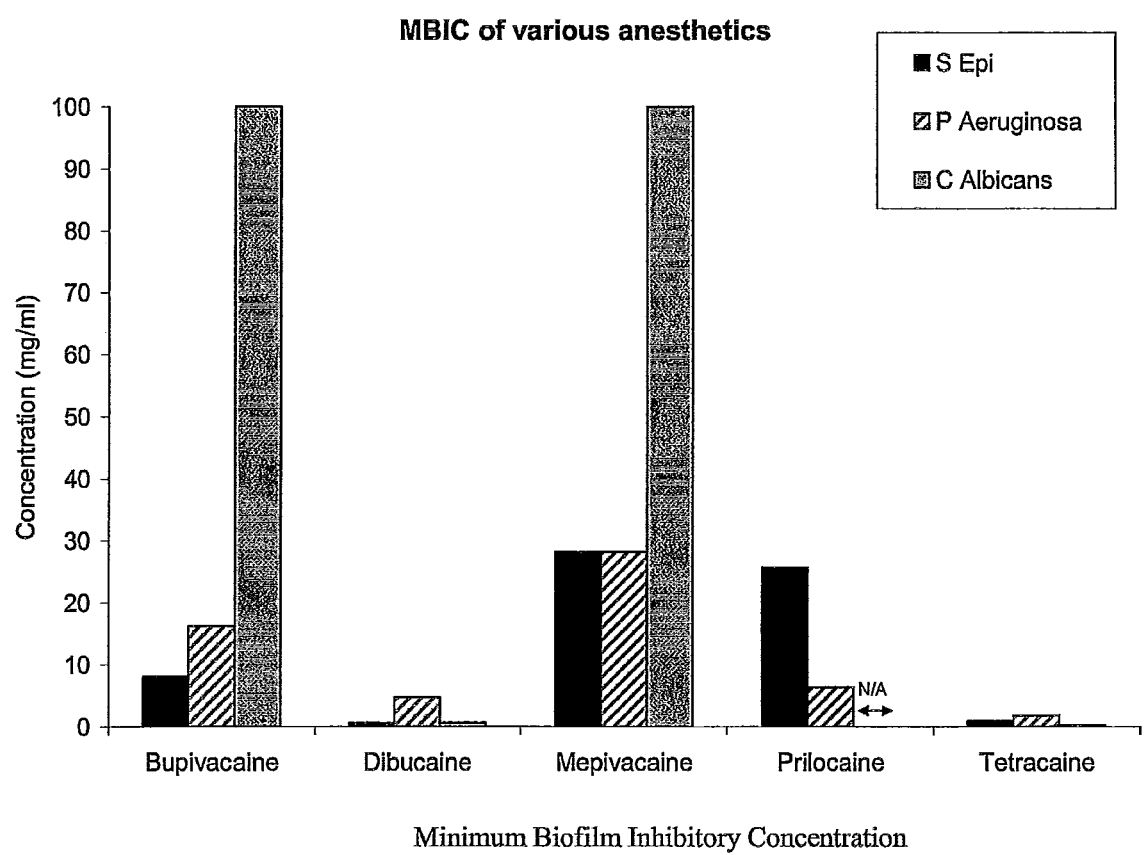
FIG. 2 is a graphical representation of the Minimum Biofilm Inhibitory Concentrations (MBIC) in mg/mL of bupivacaine, dibucaine, mepivicaine, prilocaine, and tetracaine on *Staphylococcus epidermidis, Candida albicans*, and *Pseudomonas aeruginosa*.

After the microbes entered the log phase, their concentration was checked to ensure that they had reached a minimum of $1\times10^8$ CFU/mL per a 0.5 MacFarland standard. Microbes were diluted to a concentration of $1\times10^5$ CFU/mL using a nephelometer and 200 µl, of the microbial suspensions were plated on each of the wells of a 96 well plate. The plate was incubated in a standard incubator at 37° C. for 2 hours to allow for microbial cell adhesion. Next, dilutions of the desired concentrations of antimicrobials were prepared. In a separate, blank plate, 1:2 serial dilutions were prepared with the highest concentration of the antimicrobial to the left of the plate, decreasing in concentration towards the right of the plate. For example, 170 µL of the highest concentration of an antimicrobial was dispensed in column 1 (left of plate). Each of the rest of the columns received 170 µL of saline. Column 2 received 170 µL of antimicrobial, making for a 1:2 dilution (or 50% of original concentration). Contents of Column 2 were then transferred to 3, then from 3 to 4, and so forth. Each well was supplemented with 20% media (TSB for *S. epidermidis* and *P. aeruginosa* and SDB for *C. albicans*), thereby ensuring the viability of the cells over the test time period (24 hours). Positive control wells had 20% media in saline. The bacterial plate was removed from the incubator, and bacterial suspension discarded (adhered cells remain on plate). The antimicrobial formulations identified in Table 4 were then added to the bacterial plate and incubated in a standard incubator at 37° C. for 24 hours. After this time period, solutions in the plate were discarded and plates were rinsed with 200 µL of saline. The cells were then fixed with 200 μL of 95% ethanol for 30 minutes, and allowed to air dry for 10 minutes. Next, the cells were stained for 20 minutes with 250 μL of a filtered solution of 2% crystal violet dye. The plates were then rinsed three times with water, and the 2% crystal violet dye was solubilized with 300 μL of 95% ethanol. The plates were allowed to stand for 10 minutes to complete solubilization and then the plates were read on a spectrophotometer at 570 nm absorbance, wherein high absorbance readings of >0.600 indicated microbial growth. Columns in the plate that had no growth were recorded as the Minimum Biofilm Prevention Concentration (MBIC). FIG. 2 illustrates the MBIC corresponding to the specific local anesthetics.

Specifically, when comparing the five amino amide compounds, the lowest concentration required to inhibit biofilm growth was seen with tetracaine (0.9 mg/mL for *S. epidermidis*, 1.88 mg/mL for *P. aeruginosa*, and 0.24 mg/mL for *Candida albicans*). Dibucaine exhibited the next lowest concentration required to inhibit biofilm growth with the following values: 0.59 mg/mL *S. epidermidis*, 4.794 mg/mL *P. aeruginosa*, and 0.59 mg/mL *C. albicans*. Bupivacaine exhibited the next lowest concentration required to inhibit biofilm formation. Similarly, the concentrations required for mepivacaine and prilocaine were larger than tetracaine and dibucaine. In conclusion, the present example illustrated that the local anesthetics of the present catheter locking solution, namely tetracaine, dibucaine, bupivacaine, mepivacaine, and prilocaine each inhibited biofilm growth.

Catheter Biofilm Eradication (Catheter Segment Tests)

Figure 3:
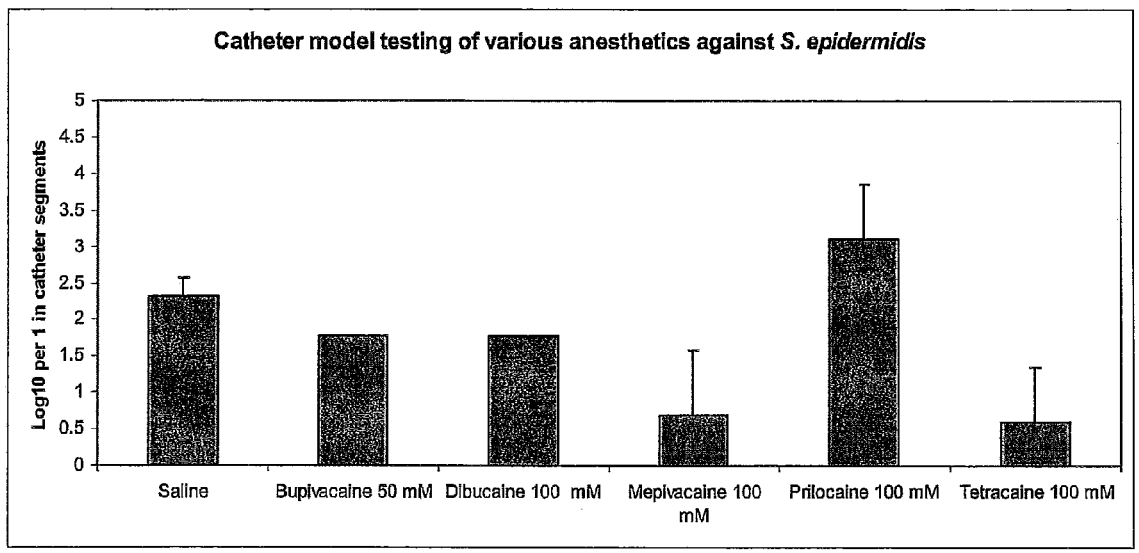
FIG. 3 is a graphical representation of catheter testing of various anesthetics against *Staphylococcus epidermidis* on silicone tubing measured by log colony-forming units/inch of catheter segment.
Figure 4:
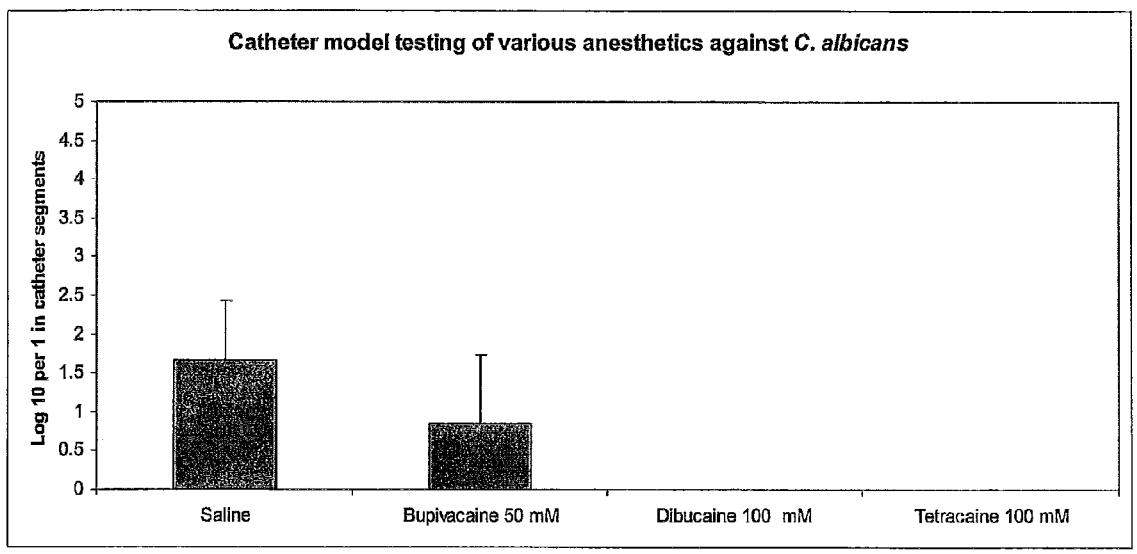
FIG. 4 is a graphical representation of catheter testing of various anesthetics against *Candida albicans* on silicone tubing measured by log colony-forming units/inch of catheter segment.

To understand the antimicrobial effects of the local anesthetics used in the lock solution of the present invention in a clinical setting, a biofilm was grown on silicone catheter-like tubing and treated with various concentrations of local anesthetics. First, a sterile silicone catheter-like tube containing 10 mL TSB media was inoculated with a BD BBL™ Qualiswab™, and placed in an incubator at 37° C. overnight. The next day, a sterile flask containing 25 mL TSB (for bacterial species) or 25 mL SDB (for fungal species) was inoculated with the cultured cells. The morning of the experiment, a new flask containing 25 mL of media was inoculated with the new overnight suspension. These steps were taken to ensure that cells were in the log phase, which for *S. epidermidis* was ~3-4 hours, and for *C. albicans* was around ~18 hrs. Using the nephelometer, concentration was checked to ensure it had reached a minimum of $1 \times 10^8$ CFU/mL per a 0.5 MacFarland standard. Microbial concentrations were adjusted to $1 \times 10^5$ CFU/mL by dilution with appropriate media. Silicone catheter-like tubing was terminally sterilized by autoclaving the tube for 45 minutes at 121° C. The sterilized catheter-like tubing was inoculated with $1 \times 10^5$ CFU/mL for 2 hours under continuous flow. Continuous flow was created by using a peristaltic pump, in which bacterial suspension was flowed through the catheter segments into a waste reservoir. After the 2 hour time period, the same set up was used to pump TSB media through the tubing for an additional 24 hours to allow biofilm to form on the walls of the catheter lumen. After 24 hours, sterilized saline was pumped through the lumen for 30 minutes to rinse the catheters. Catheters were then cut into 1 inch segments using sterile techniques. Catheter segments were dropped into sterile tubes containing 4 mL of antimicrobials, and incubated in a 37° C. incubator shaker for 1 hour. Segments were removed from treatment tubes and placed into new tubes filled with 6 mL of sterile saline. Each segment was swabbed with a sterile swab and both the tube and the swab were sonicated (Ultrasonic cleaner VWR Model 250T) for 3 minutes. Tubes and swabs were then vortexed (Fisher Scientific Vortex Mixer #02-215-365) for 30 seconds each. One hundred microliters of suspension was plated onto TSB agar plates (SDB for fungal species). The remaining 5.9 mL of suspension was passed through 0.4 μm filters and filters were placed on TSB plates. This step was taken to ensure that all possible bacteria were being recovered. All TSB plates were then incubated at 37° C. in a static incubator for 24-48 hours, at which time colony forming units were counted. FIGS. 3 and 4 show the eradication of *Staphylococcus epidermidis* biofilm and *Candida albicans* biofilm on silicone catheter segments, respectively in a 1 inch section of test tubing. The graphs show, in the $Log_{10}$ scale, the control samples for both species, and the counts obtained on treated segments. For *S. epidermidis*, mepivacaine at 28 mg/mL and tetracaine at 30 mg/mL eradicated the established biofilm, exhibiting a 1.6 and 1.7 Log reduction, respectively. Bupivacaine (16 mg/mL) and Dibucaine (38 mg/mL) had slightly lower reductions, each exhibiting an approximate 0.5 Log reduction. Prilocaine had minimal antimicrobial effect. For *C. albicans*, dibucaine (38 mg/mL) and tetracaine (30 mg/mL) completely eradicated the established biofilm, with bupivacaine having close to a 1 Log reduction. Specifically, the present catheter biofilm eradication experiments illustrate how the local anesthetics of the present catheter locking solution, namely, bupivacaine, dibucaine, prilocaine, and tetracaine, effectively reduce microbes on silicone catheter-like tubing similar to those used in a clinical setting.

Viscosifying Agent Testing

Figure 6:
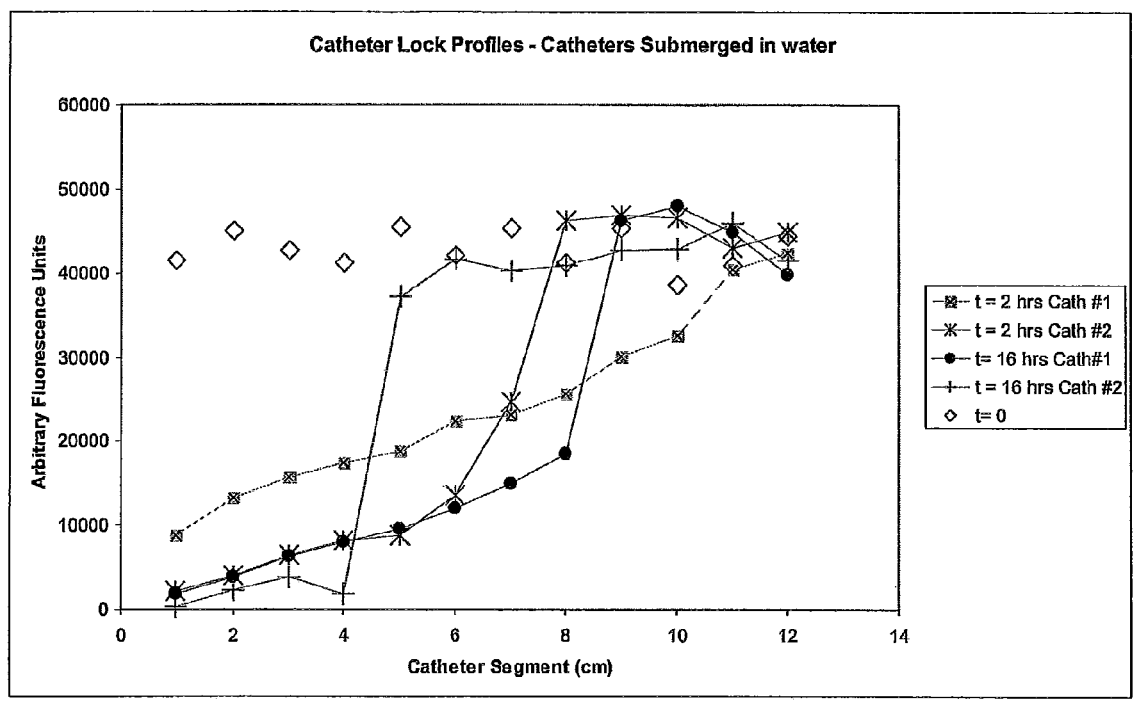
FIG. 6 is a graphical representation of the arbitrary fluorescence units measured on various locations of catheter segments at different times when the catheters are submerged in water.
Figure 7:
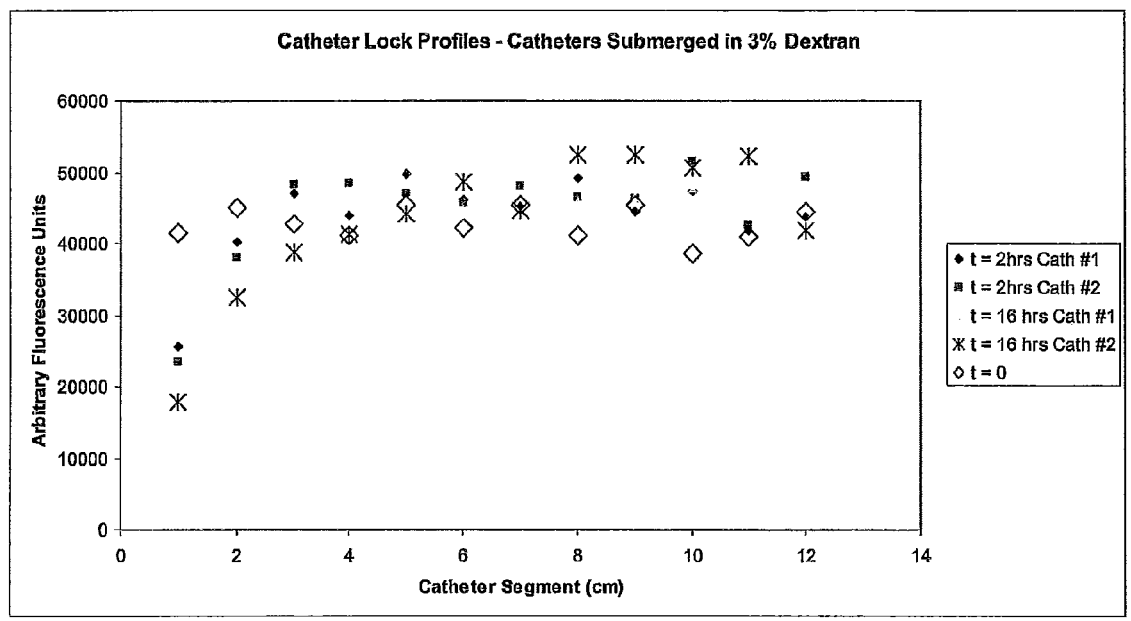
FIG. 7 is a graphical representation of the arbitrary fluorescence units measured on various locations of catheter segments at different times when the catheters are submerged in a 3% dextran solution.

As previously indicated, various viscosifying agents, including polyethylene glycol, glycerin, polygeline, dextran, or some mixture of polyethylene glycol, glycerin, polygeline, and dextran can be utilized in the catheter locking solution of the present invention. An experiment was conducted to understand the range of a viscosifying agent that would be preferred in the catheter lock solution of the present invention. A 6% dextran solution was made by mixing 3 g of dextran with 50 mL of water. The solution was vortexed and stirred until dissolved. Next, 4.27 mL of the solution was mixed with 10 mL of bovine serum, to mimic blood viscosity (SD solution). Next, from a 1000 μg/mL concentration of pure fluorescent dye Alexa Flour® 488 (Molecular Probes #A20-000), 10 mL of a 50 μg/mL fluorescent concentration was made with an antimicrobial agent having a viscosity close to water. Next, four silicone PICC Catheters (BD First PICC 16 g (5 Fr)×65 cm ID/OD0.76/1.70 (BD #384158)) were prepared by removal of their guide wire, and by cutting of connector devices, so that the catheters were stretched out to 16 cm. The catheters were then filled with the fluorescent antimicrobial solution and clamped on one end, as would be done in clinical practice. The entire length of the catheters were then submerged in either a 6% dextran solution (having a viscosity similar to blood) or in water. The catheters filled with the fluorescent antimicrobial solution were left submerged for either 2 hours or overnight (16 hours). After the desired time points, catheters were retrieved from their set up and processed. The catheters were stretched out onto a hydrophobic surface (such as a sheet of Teflon). Next, using a razorblade, catheter segments were cut at each of the 1 cm graduations found on the catheter surface. Each segment was placed into a centrifuge tube containing 1 mL of water. Each tube was then vortexed for 10 seconds, and 200 μL from each solution was placed into a 96 well plate, with three replicates per tube. Both FIGS. 6 and 7 show the results as the y-axis showing arbitrary fluorescence units, and the x-axis showing the number centimeter marker of the catheter, with the first segment being the furthest from the catheter clamp. As shown in FIG. 6 there is a gradual leakage of the contents of the catheter (simulated lock solution) when catheters are submerged in water. Even after 2 hours of submersion, we can see that at 6 cm from the tip, there is a considerably less amount of fluorescence recovered from the segments, indicating a loss in the catheter lock solution. By contrast, as shown in FIG. 7, even after 16 hours, there is a slight loss of catheter concentration. Control data (catheters that were not submerged) showed arbitrary fluoresence units in the 45,000 range, indicated on the graphs by an open diamond. The conclusion for this work is that viscosifying agents, if included in the lock solutions, should have a lower viscosity than blood. From this data we conclude that the viscosifying agent in the present lock solution may be less than 3-4 MPa·s, so that catheter contents will remain in the catheter lumen. Particularly, the present example illustrates how the viscosifying agent of the present catheter locking solution increases the viscosity of the lock solution such that it is closer to that of blood, and therefore the lock solution may be prevented from aspirating from the catheter lumen, and into the surrounding blood environment.

Anticoagulation Testing

The local anesthetics have also been shown to have an anticoagulant effect. In order to understand what the working concentration range could be for the anesthetics tested, a Sheep's Plasma Clotting Assay was performed. This test is based on the United States Pharmacopeia (USP) standard test for coagulation and is often used to understand heparin potency. The anesthetics were compared to a heparin standard, in order to have an idea of the equivalence of the local anesthetics in comparison to heparin. Sheep plasma was thawed in a water bath set to 37° C. To facilitate thawing, the plasma in the bottle was inverted every 15 minutes. The plasma was thawed after about 45-60 minutes. The thawed sheep plasma was filtered through glass wool or filtered into a clean glass beaker or flask, to remove particulate matter and to activate it. About 70-80 mL of filtered sheep plasma was collected. Next, a set of test tubes were prepared (VWR Disposable 13×100-mm) in a 6×12 rack. Ten test tubes were needed for each test solution including ten test tubes for the heparin standard. Each of the experiments was conducted three times to show the consistency of anticoagulant effect. For each test solution, every (10) test tube received different volumes of 0.9% NaCl. Particularly, the volumes ranged from 520 µL in the first test tube to 340 µL in the tenth test tubes, wherein each of test tubes two (2) through ten (10) had a 20 µL decrease in volume. Next, the local anesthetics were added, namely, tetracaine at 30 mg/mL, dibucaine at 30 mg/mL, and bupivacaine at 38 mg/mL. Each of the ten test tubes received different volumes of test solutions, starting with 280 µL and increasing in volume by 20 µL until reaching a volume of 460 µL at the tenth tube. The total volume of saline and test solutions in each of the tubes was 800 µL. A standard solution, namely, USP heparin sodium standard, was also prepared in the same way, with the starting concentration of heparin being 5.6 U/mL. Next, 1 mL of sheep plasma for heparin assay (Bio-Supplies, Inc, P-SPR-1500) was pipetted into each tube, and the rack was gently shaken to ensure mixing. Two hundred µL of a 1% $CaCl_2$ solution was placed into each tube. The total volume for each tube is 2 mL. Each tube was capped with a VWR Plug-type cap, and contents of each tube were inverted six times to ensure that the entire inner wall of each tube was wet. Tubes were incubated for 1 hour at room temperature. After the 1 hour time period, the extent of clotting in each tube was determined by gently shaking each individual test tube (tapping the end gently is acceptable) and then tilting the tube to observe a clot both vertically and horizontally. The degree to which each tube developed a clot was recorded using the following criteria (per the USP Standard) for the visual inspection of the tubes:

0% Clotting=No apparent clot formed.
25% Clotting=Small observable clot with mostly liquid. Clot is very mobile.
50% Clotting=Plasma is completely clotted but mobile.
75% Clotting=Clot is not mobile but liquid is still present.
100% Clotting=Clot is not mobile and no liquid is present.

A summary of the results of this testing are shown in Table 5 and are shown per test formulation.

TABLE 5

Anticoagulation for local anesthetics in the lock solution of the present invention and their equivalence to Heparin

| Anesthetics | Replicate | 50% clotting range (mg/mL) | Equivalence to Heparin (U/mL) |
|---|---|---|---|
| Tetracaine | 1 | 5.1-5.4 | 6.24 |
|  | 2 | 5.4 | 6.24 |
|  | 3 | 5.4 | 6.06 |
| Bupivacaine | 1 | N/A | N/A |
|  | 2 | N/A | N/A |
|  | 3 | N/A | N/A |
| Dibucaine | 1 | 5.1-5.4 | 6.23 |
|  | 2 | 5.1-5.4 | 6.23 |
|  | 3 | 5.1-5.4 | 6.23 |

Because of the testing protocol, starting concentrations of anesthetics were diluted from the original formulation. Calculations can be made to compare the efficacy of these anesthetics to the standard anticoagulant heparin by calculating the point at which both standard and test samples yield 50% clotting. Using this calculation, the anesthetic concentration can be referenced back to a measure of U/mL of heparin equivalence. As an example of how these were calculated, we see that Rep 1 in the heparin standard had a 50% coagulation at 370 µL volume of anesthetic. Tetracaine Rep 1 had 50% coagulation at a volume of 350 µL. Assuming a heparin equivalent potency of 5.9 U/mL (starting concentration of heparin), we then calculate that tetracaine at a final concentration between 5.1 and 5.4 mg/mL is equivalent to 6.25 U/mL of heparin (i.e., (370 µL/350 µL)×5.9)). For bupivacaine, values obtained for the coagulation testing showed that the concentrations tested yielded a 75% coagulation at all concentrations tested. Dibucaine showed a very consistent result, yielding an equivalent to heparin of 6.23 U/ml, in three out of the three experiments conducted, and also between the concentrations of 5.1-5.4 mg/ml. Therefore, the present invention shows the efficacy of the local anesthetics of the catheter locking solution of the present invention, namely, tetracaine, dibucaine, and bupivacaine, to prevent and inhibit coagulation.

One of the major advantages of the claimed invention, as shown by the examples, is that the claimed catheter locking solution includes a local anesthetic and a viscosifying agent, whereby the local anesthetic provides both antimicrobial and anticoagulation properties. Particularly, the examples illustrate that a single local anesthetic can have dual functionality as an antimicrobial agent and an anticoagulation agent. This is a significant improvement over current attempts to maintain catheters patent and free of infection, in which antibiotics and other chelators are utilized simultaneously. Additionally, the viscosifying agent of the present catheter locking solution increases the viscosity of the lock solution such that it is closer to that of blood, and therefore the lock solution may be prevented from aspirating from the catheter lumen and into the surrounding blood environment. Therefore, the catheter locking solution of the present invention addresses the problems previously associated with catheter lock solutions and further provides antimicrobial protection as well as coagulation inhibition by providing a catheter locking solution including a local anesthetic and viscosifying agent.

While specific embodiments of the invention have been described in detail, it will be appreciated by those skilled in the art that various modifications and alternatives to those details could be developed in light of the overall teachings of the disclosure. The presently preferred embodiments described herein are meant to be illustrative only and not limiting as to the scope of the invention which is to be given the full breadth of the appended claims and any and all equivalents thereof.

The invention claimed is:

1. A catheter locking solution comprising:
a local anesthetic selected from the group consisting of dibucaine, tetracaine, and a combination thereof, in an amount effective to reduce microbial growth and coagulation in an implanted catheter; and
a viscosifying agent, the catheter locking solution having a viscosity of less than or equal to 4 mPa·s.

2. The catheter locking solution of claim 1, further comprising an additional local anesthetic, different from the local anesthetic, selected from the group consisting of an amino amide; an amino ester; an aminoacylanilide; an aminoalkyl benzoate; an amino carbonate; an N-phenylamidine compound; an N-aminoalkyl amide; an aminoketone, or combinations and mixtures thereof.

3. The catheter locking solution of claim 1, further comprising an additional local anesthetic, different from the local anesthetic, selected from the group consisting of dibucaine, tetracaine, bupivacaine, ropivacaine, etidocaine, lidocaine, prilocaine, procaine, novocaine, choloroprocaine, propoxycaine, chlorocaine, mepivacaine, xylocaine, benzocaine, chloroprocaine, cyclomethycaine, dimethocaine, popoxycaine, proparacaine, articaine, carticaine, levobupivacaine, piperocaine, trimecaine, hexylcaine, benoxinate, butucaine, diperodon, phenacaine, falicaine, dyclonine, pramoxine, dimethisoquien, and combinations and mixtures thereof.

4. The catheter locking solution of claim 1, wherein the local anesthetic is present in an amount of 0.05 mg/mL-100 mg/mL.

5. The catheter locking solution of claim 1, wherein the local anesthetic is present in an amount of 0.24 mg/mL-28.2 mg/mL.

6. The catheter locking solution of claim 1, wherein the viscosifying agent is selected from the group consisting of polyethylene glycol, glycerin, polygeline, or any mixture thereof.

7. The catheter locking solution of claim 1, wherein the local anesthetic is tetracaine and the viscosifying agent is polyethylene glycol.

8. The catheter locking solution of claim 1, wherein the local anesthetic is dibucaine and the viscosifying agent is polyethylene glycol.

9. The catheter locking solution of claim 1, further comprising an antimicrobial agent other than the local anesthetic.

10. The catheter locking solution of claim 1, further comprising an anticoagulation agent other than the local anesthetic.

11. A pre-filled syringe comprising a syringe containing a locking solution, said locking solution comprising:
a local anesthetic selected from the group consisting of dibucaine, tetracaine, and a combination thereof, in an amount effective to reduce microbial growth and coagulation in an implanted catheter; and
a viscosifying agent,
the catheter locking solution having a viscosity of less than or equal to 4 mPa·s.

12. The pre-filled syringe of claim 11, further comprising an additional local anesthetic, different from the local anesthetic, selected from the group consisting of an amino amide; an amino ester; an aminoacylanilide; an aminoalkyl benzoate; an amino carbonate; an N-phenylamidine compound; an N-aminoalkyl amide; an aminoketone, or combinations and mixtures thereof.

13. The pre-filled syringe of claim 11, further comprising an additional local anesthetic, different from the local anesthetic, selected from the group consisting of dibucaine, tetracaine, bupivacaine, ropivacaine, etidocaine, lidocaine, prilocaine, procaine, novocaine, choloroprocaine, propoxycaine, chlorocaine, mepivacaine, xylocaine, benzocaine, chloroprocaine, cyclomethycaine, dimethocaine, popoxycaine, articaine, carticaine, levobupivacaine, piperocaine, trimecaine, hexylcaine, benoxinate, butucaine, proparacaine, diperodon, phenacaine, falicaine, dyclonine, pramoxine, dimethisoquien, and combinations and mixtures thereof.

14. The pre-filled syringe of claim 11, wherein the local anesthetic is present in an amount of 0.05 mg/mL-100 mg/mL.

15. The pre-filled syringe of claim 11, wherein the local anesthetic is present in an amount of 0.24 mg/mL-28.2 mg/mL.

16. The pre-filled syringe of claim 11, wherein the viscosifying agent is selected from the group consisting of polyethylene glycol, glycerin, polygeline, or any mixture thereof.

17. The pre-filled syringe of claim 11, wherein the local anesthetic is tetracaine and the viscosifying agent is polyethylene glycol.

18. The pre-filled syringe of claim 11, wherein the local anesthetic is dibucaine and the viscosifying agent is polyethylene glycol.

19. The pre-filled syringe of claim 11, further comprising an antimicrobial agent other than the local anesthetic.

20. The pre-filled syringe of claim 11, further comprising an anticoagulation agent other than the local anesthetic.

21. A catheter comprising a tube defining a lumen therethrough, wherein at least a portion of the lumen is infused with a catheter locking solution, said catheter locking solution comprising:
a local anesthetic selected from the group consisting of dibucaine, tetracaine, and a combination thereof, in an amount effective to reduce microbial growth and coagulation in an implanted catheter; and
a viscosifying agent,
the catheter locking solution having a viscosity of less than or equal to 4 mPa·s.

22. The catheter of claim 21, wherein the catheter locking solution further comprises an additional local anesthetic, different from the local anesthetic, selected from the group consisting of an amino amide; an amino ester; an aminoacylanilide; an aminoalkyl benzoate; an amino carbonate; an N-phenylamidine compound; an N-aminoalkyl amide; an aminoketone, or combinations and mixtures thereof.

23. The catheter of claim 21, wherein the catheter locking solution further comprises an additional local anesthetic, different from the local anesthetic, selected from the group consisting of dibucaine, tetracaine, bupivacaine, ropivacaine, etidocaine, lidocaine, prilocaine, procaine, novocaine, choloroprocaine, propoxycaine, chlorocaine, mepivacaine, xylocaine, benzocaine, chloroprocaine, cyclomethycaine, dimethocaine, popoxycaine, articaine, carticaine, levobupivacaine, piperocaine, trimecaine, hexylcaine, benoxinate, butucaine, proparacaine, diperodon, phenacaine, falicaine, dyclonine, pramoxine, dimethisoquien, and combinations and mixtures thereof.

24. A catheter locking solution comprising:
a local anesthetic having anticoagulant and antimicrobial activity, wherein the local anesthetic is tetracaine; and
a viscosifying agent, wherein the viscosifying agent is polyethylene glycol,
wherein the local anesthetic is present in an amount of 0.24 mg/mL-28.2 mg/mL, and
the catheter locking solution having a viscosity of less than or equal to 4 mPa·s.

25. A catheter locking solution comprising:
a local anesthetic having anticoagulant and antimicrobial activity, wherein the local anesthetic is dibucaine; and
a viscosifying agent, wherein the viscosifying agents is polyethylene glycol, wherein the local anesthetic is present in an amount of 0.24 mg/mL-28.2 mg/mL,
the catheter locking solution having a viscosity of less than or equal to 4 mPa·s.

26. A method of reducing microbial activity and coagulation in a catheter, the method comprising:
providing a catheter having an interior surface and an exterior surface; and
infusing, into at least a portion of the interior surface, a catheter locking solution comprising a local anesthetic selected from the group consisting of dibucaine, tetracaine, and a combination thereof, in an amount effective to reduce microbial growth and coagulation in an implanted catheter and a viscosifying agent.

27. The method of claim 26, further comprising reinfusing said interior surface of said catheter with the catheter locking solution after a designated time, wherein said designated time is less than one week.

28. The method of claim 26, wherein the interior surface of the catheter has an internal volume and said infusing includes infusing the interior surface with an amount of the lock solution sufficient to fill between about 80% and 100% of the internal volume of the interior surface.

29. The method of claim 26, wherein the interior surface of the catheter is infused between 1 and 1000 times.

* * * * *

UNITED STATES PATENT AND TRADEMARK OFFICE
CERTIFICATE OF CORRECTION

PATENT NO. : 9,248,093 B2
APPLICATION NO. : 12/797336
DATED : February 2, 2016
INVENTOR(S) : John J. Kelley, III et al.

Page 1 of 1

It is certified that error appears in the above-identified patent and that said Letters Patent is hereby corrected as shown below:

On the Title Page of the Patent, Column 2, OTHER PUBLICATIONS, Line 9, delete "Pharmcay" and insert -- Pharmacy --

In the Claims

Column 17, Line 32, Claim 3, delete "choloroprocaine," and insert -- chloroprocaine, --

Column 17, Line 35, Claim 3, delete "popoxycaine," and insert -- propoxycaine, --

Column 17, Line 37, Claim 3, delete "butucaine," and insert -- butacaine, --

Column 17, Line 38, Claim 3, delete "dimethisoquien," and insert -- dimethisoquin, --

Column 18, Line 14, Claim 13, delete "choloroprocaine," and insert -- chloroprocaine, --

Column 18, Line 17, Claim 13, delete "popoxycaine," and insert -- propoxycaine, --

Column 18, Line 18, Claim 13, delete "butucaine," and insert -- butacaine, --

Column 18, Line 20, Claim 13, delete "dimethisoquien," and insert -- dimethisoquin, --

Column 18, Line 64, Claim 23, delete "choloroprocaine," and insert -- chloroprocaine, --

Column 18, Line 66, Claim 23, delete "popoxycaine," and insert -- propoxycaine, --

Column 19, Line 1, Claim 23, delete "butucaine," and insert -- butacaine, --

Column 19, Line 2, Claim 23, delete "dimethisoquien," and insert -- dimethisoquin, --

Signed and Sealed this
Thirty-first Day of May, 2016

Michelle K. Lee
*Director of the United States Patent and Trademark Office*